United States Patent [19]
Oberlander

[11] Patent Number: 5,154,189
[45] Date of Patent: Oct. 13, 1992

[54] METHOD FOR REPAIRING A TORN MENISCUS

[76] Inventor: Michael A. Oberlander, 2007 Commonwealth Ave., Auburndale, Mass. 02166

[21] Appl. No.: 759,032

[22] Filed: Sep. 4, 1991

Related U.S. Application Data

[63] Continuation of Ser. No. 672,895, Mar. 21, 1991, abandoned, which is a continuation of Ser. No. 511,445, Apr. 18, 1990, Pat. No. 5,002,562, which is a continuation of Ser. No. 201,841, Jun. 3, 1988, abandoned.

[51] Int. Cl.⁵ .............................................. A61B 17/00
[52] U.S. Cl. .................................... 128/898; 606/142; 606/216
[58] Field of Search ................ 128/898; 606/139, 142, 606/216, 219, 221, 223

[56] References Cited

U.S. PATENT DOCUMENTS

| | | | |
|---|---|---|---|
| 4,602,635 | 7/1986 | Muihoiian et al. | 606/148 |
| 4,669,473 | 6/1987 | Richards et al. | 606/220 |
| 4,781,190 | 11/1988 | Lee | 606/139 |
| 4,923,461 | 5/1990 | Caspari et al. | 606/148 |
| 4,983,176 | 1/1991 | Cushman et al. | 606/216 |

Primary Examiner—Stephen C. Pellegrino
Assistant Examiner—Gary Jackson
Attorney, Agent, or Firm—Thomas R. Bremer

[57] ABSTRACT

A method for repairing tears in fibrocartilage and soft tissue. The clip has a pair of opposed legs formed of rigid biodegradable material. Each leg has at least one barb for easily penetrating the cartilage and soft tissue, and for opposing withdrawal from it. The legs are interconnected by a flexible section that is also biodegradable. The instrument for applying these clips has a pair of opposed jaws, each with at least one notch for holding the barbs of the clip. The jaws are biased apart in a normally open position and are interconnected to an actuating handle. The instrument further includes a device which closes the jaws when the handles are moved a first way relative to one another and opens them when the handles are moved the other way.

11 Claims, 4 Drawing Sheets

METHOD FOR REPAIRING A TORN MENISCUS

This is a continuation of co-pending application Ser. No. 07/672,895, filed on Mar. 21, 1991 now abandoned, which is a continuation of pending U.S. application Ser. No. 07/511,445, filed Apr. 18, 1990 now U.S. Pat. No. 5,002,562, which is a continuation of application Ser. No. 07/201,841 filed Jun. 3, 1988, now abandoned.

FIELD OF INVENTION

This invention relates to a method for inserting a clip used to repair menisci and soft tissue.

BACKGROUND OF INVENTION

Tears in fibrocartilage and soft tissue, especially peripheral meniscal tears, are reatively difficult to repair. Typically, a tear in the vascular region of the meniscus is sutured using arthroscopic techniques. The instrument may be inserted through small incisions which serve as anterior knee portals. Sutures on long needles are then passed through a meniscal repair instrument and through the meniscus. An incision is made in the back of the knee to permit the surgeon to pull the needles and suture out, and to tie the suture over the posterior joint capsule. This technique reapproximates the torn edges of the meniscus and allows for healing.

Although effective, this repair technique requires a surgeon skilled in arthroscopic meniscal repair. The technique is also relatively time consuming and more invasive than it need be, as it requires a second, posterior incision that increases the risk of infection and neurovascular damage. As a result, few surgeons will attempt meniscal repair, choosing instead to simply remove the damaged portion of the meniscus. The problem with this approach is that meniscal removal can cause increased stress on the articular cartilage, which may then lead to degenerative arthritis.

Surgical clips are often easier to insert than sutures. However, most clips are not biodegradable, and occasionally a second operation must be performed to remove the clip once the tissue has healed. Another disadvantage of these clips is that they are not well suited for meniscal and soft tissue repair, as they are typically metallic, relatively large, and may protrude from the tissue and cause joint irritation. Thus, although arthroscopic clips can be inserted through a single incision, they have typically not been used for repair of peripheral meniscal tears nor for arthroscopic repair of soft tissue.

SUMMARY OF INVENTION

It is therefore an object of this invention to provide a method for inserted arthroscopic clip for operative arthroscopic repair of menisci and soft tissue.

It is a further object of this invention to provide a method for inserting an arthroscopic clip which allows a surgeon not trained in meniscal repair to reapproximate torn meniscal tissue.

It is a further object of this invention to provide a method and an arthroscopic clip which decrease risk of neurovascular damage to the patient.

It is a further object of this invention to provide a method and an arthroscopic clip which decrease operative time, by facilitating the operative procedure.

It is a further object of this invention to provide a method and an arthroscopic clip that do not require a second operation to remove the clip.

It is a further object of this invention to provide a method and an arthroscopic surgical clip with legs that remain buried in the tissue and do not irritate surrounding tissue.

This invention results from the realization that arthroscopic surgical clips for repairing tears in menisci and soft tissue can be improved dramatically by providing a biodegradable clip with rigid, barbed legs interconnected by a flexible section that is inserted in the tissue with an arthroscopic tool and anchors itself in the tissue to approximate the tear.

This invention features an arthroscopic clip and insertion tool for repair of tears in fibrocartilage and soft tissue. The clip has a pair of opposed legs formed of rigid biodegradable material interconnected by a flexible, biodegradable section. Each leg has at least one barb that allows the clip to be easily inserted into the tissue being repaired but keeps the clip from working out of the tissue. The legs of the clip are preferably curved inwardly toward each other, and each leg preferably has more than one barb on its outer side. A preferred material for the legs is a polyglycolic acid polymer.

The arthroscopic instrument for applying the barbed arthroscopic clips has a pair of opposed jaws that are preferably offset to allow them to overlap when closed. Each jaw has at least one notch for holding the barbs of the clip. These specialized jaws tightly hold the clips in place until they are fully inserted, which allows the physician to place them in exactly the right position and to exactly the right depth before they are released. The instrument includes a biasing means for separating the jaws in a normally open position, which is the position in which the jaws remain as the clip insertion begins. The jaws are connected to a handle by a member such as a tubular member. The instrument also includes means for closing the jaws when the two handle members are moved one way relative to one another and opening the jaws when the handles are moved another way.

Preferably, the actuating handle is normally biased open, and the means for closing the jaws closes them when the handle members are squeezed together and opens them when the handle members are spread apart. The means for closing may include means for pulling the jaws together as the handle members are moved. The jaws may be disposed at an angle to the tubular member to facilitate clip insertion. Additionally, the tips of the jaws are preferably sharpened to facilitate clip insertion.

Preferably, the instrument further includes means for releasing the clip from the jaws so it stays in place when the jaws are opened. The means for releasing may include means for releasably holding at least one barb of the clip, and may further include means for selectively releasing the means for releasably holding the barb from the barb. Means for actuating the means for selectively releasing, which may include an actuating member or switch on the handle of the instrument, are also preferably included.

In use, the clip is placed in the jaws with the barbs in the jaw notches. This holds the clip tightly in place as it is inserted. To insert the clip, the physician begins pushing the jaws into the tissue, squeezing the handle members at the same time. The sharpened tips of the jaws pierce the tissue and, as it is inserted, the legs are moved together. Preferably, the jaws of the instrument overlap when they are completely closed. This overlapping causes the legs of the clip to overlap when it is completely inserted in the tissue. The switch on the handle then is moved upward to release the clip from the jaws. The barbs on the clip legs then hold the clip in position once the jaws are opened up and pulled away from the clip. When the instrument is removed from the tissue, the clip remains with its legs completely embedded within the tissue with only the flexible, non-irritating interconnecting member protruding from the tissue surface. Since the clip is biodegradable, it slowly dissolves as the tissue heals itself, and there is no need for a second operation to remove the clips.

DISCLOSURE OF PREFERRED EMBODIMENT

Other objects, features, and advantages will occur from the following description of a preferred embodiment and the accompanying drawings, in which.

An arthroscopic clip for arthroscopic repair of tears in fibrocartilage and soft tissue which is especially useful for meniscal repair according to this invention may be accomplished by providing a clip with a pair of opposed legs formed of a rigid biodegradable material. Each leg has at least one barb that allows the clip to easily penetrate the tissue being repaired and oppose withdrawal from it. The legs are interconnected by a flexible, non-irritating biodegradable section that allows the clip to bend.

Preferably, the legs of the clip are curved inwardly toward each other, and the barbs are on the outside of the legs. The barbs may alternatively be on the insides of the legs. These legs are preferably made from a polyglycolic acid polymer. The flexible interconnecting section can be formed of suture material or another relatively soft, flexible material that allows the clip to bend as it is inserted so that the clip can overlap inside the tissue being approximated. The clip is ideally suited for reapproximating peripheral meniscal tears.

The arthroscopic instrument for applying the clips includes a pair of opposed jaws each having at least one notch for holding the barbs of the clip. This allows the clip to be tightly held in place in the jaws until it is completely inserted in the tissue being repaired. The jaws are biased apart in a normally open position, and they are attached to the handle by a tubular member. The actuating handle has opposed handle members and is also connected to the jaws by means such as a pair of wires or an actuating member which close the jaws when the handle is squeezed. The instrument may have jaws preset at different angles to further facilitate insertion of the clip. The jaws may also have sharpened tips to facilitate insertion. In addition, the jaws are preferably offset so they overlap when closed, so that the legs of the clip overlap inside the tissue to better approximate the torn tissue.

Figure 1:
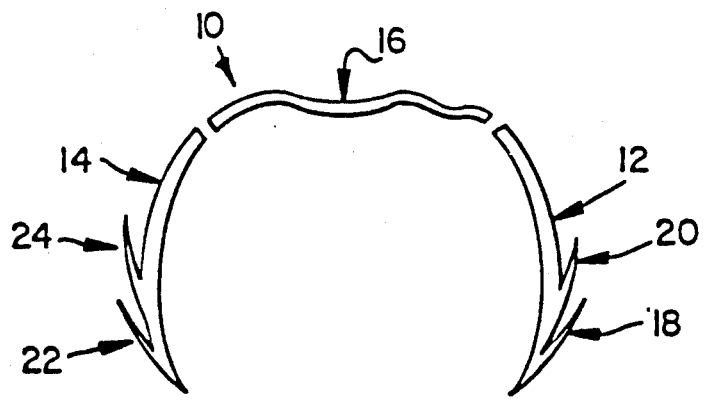
FIG. 1 is an elevational view of an arthroscopic clip for repairing tears in cartilage and soft tissue according to this invention.

There is shown in FIG. 1 one embodiment of an arthroscopic clip 10 for repair of tears in cartilage and soft tissue according to this invention. The clip is especially useful for repairing peripheral meniscal tears, partial or small rotator cuff tears, labrum tears in shoulder arthroscopy, and retinacular repair after patellar dislocations. The clip has barbed legs 12 and 14 with barbs 18 and 20, and 22 and 24, respectively. Legs 12 and 14 are formed of a rigid biodegradable material which may be a polyglycolic acid polymer. Legs 12 and 14 are interconnected by biodegradable, flexible, non-irritating section 16 which may be a suture material. Section 16 bends to allow the legs to move in toward each other and overlap as they are pushed into the tissue. Once inserted, the clips hold the tissue in place long enough for it to heal, and slowly dissolve so the patient does not have to undergo a second operation for clip removal.

Figure 2:
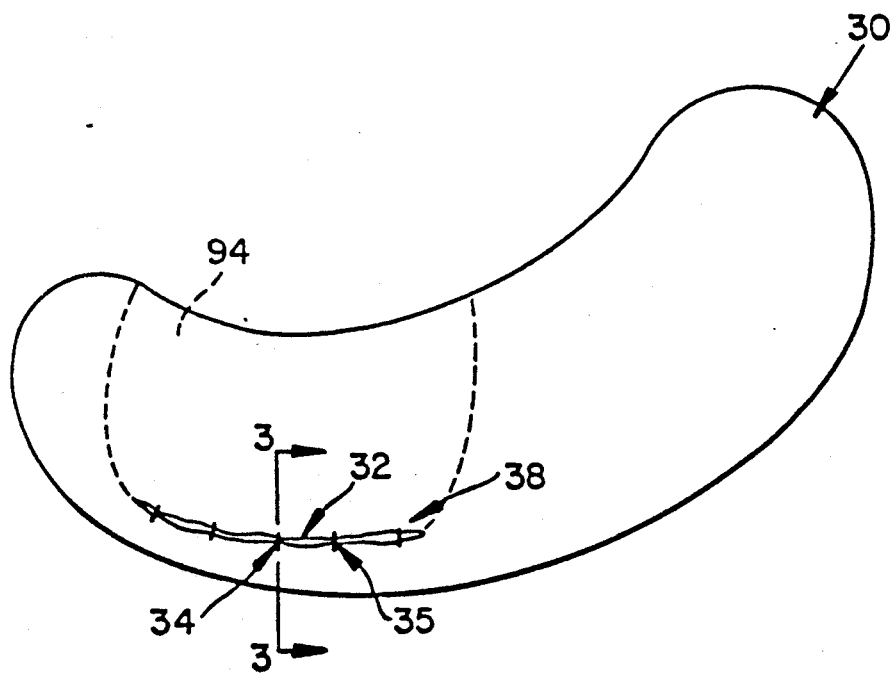
FIG. 2 is a diagram of a meniscular tear reapproximated by three of the clips of FIG. 1.

Peripheral meniscal tear 32, FIG. 2, is a relatively small tear that is considered repairable. Because of the problems to date with meniscal surgery, portion 94 of meniscus 30, encompassed by the dashed lines, has often been removed when a peripheral tear is found. Since meniscal removal may cause increased stress on the articular cartilage and secondarily lead to degenerative arthritis, repair is far superior to removal. By using clips such as clips 34, 35, and 38, the meniscus can be successfully repaired with a single operative procedure.

Figure 3:
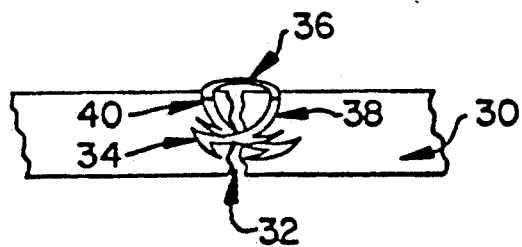
FIG. 3 is a cross-sectional view taken along line 3—3 of FIG. 2.

Clip 34 is shown embedded in meniscus 30 in FIG. 3. Clip 34 includes barbed legs 38 and 40 interconnected by flexible section 36. When inserted, legs 38 and 40 overlap, which causes the legs to approximate the tissue and minimize gap 32 through which fibrous tissue will form and thus further enhance healing. When the clip is inserted as shown, only the soft connecting portion 36 protrudes from the tissue and is exposed to the articular cartilage. Since this soft material does not irritate the surrounding articular cartilage, the patient does not need to have the joint rigidly immobilized for a long period of time. This is an additional advantage of the arthroscopic clip according to this invention.

Figure 4A:
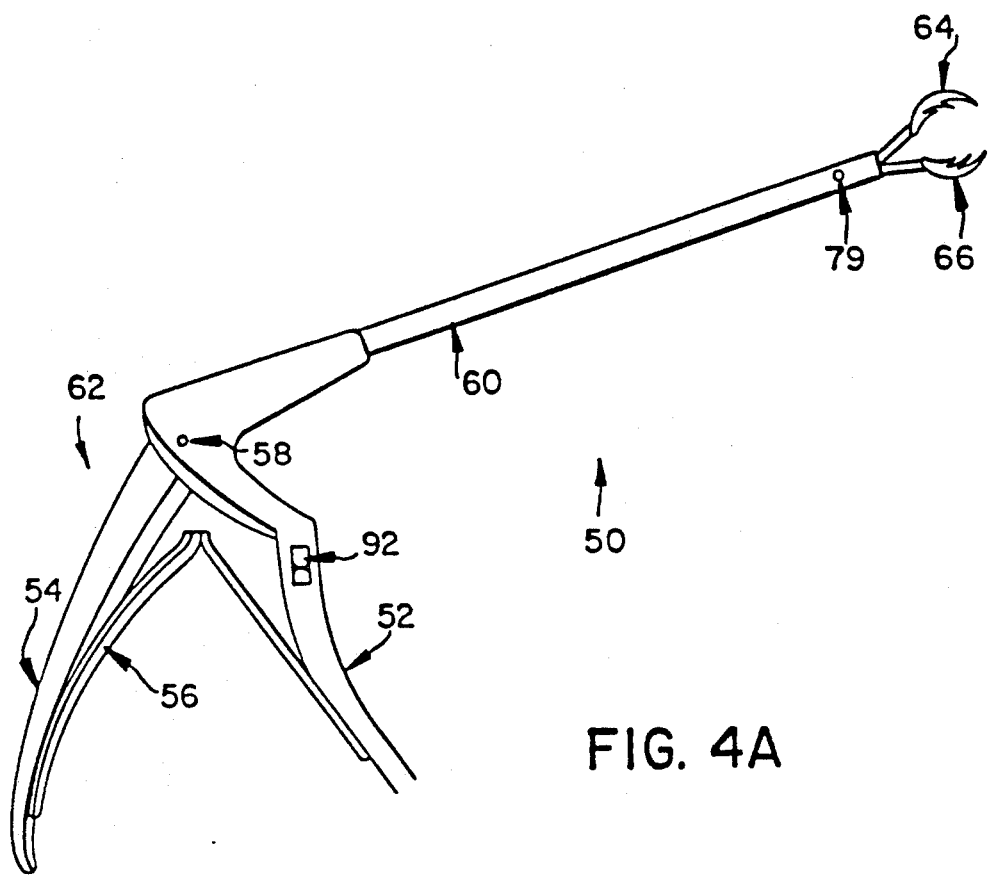
FIG. 4A is an axonometric view of an arthroscopic tool for inserting the clip of FIG. 1 according to this invention.

The arthroscopic instrument for applying the barbed clips is shown in FIG. 4A. Instrument 50 includes notched jaws 64 and 66 made of spring steel formed to keep them in a normally open position. Tubular member 60 interconnects jaws 64 and 66 to handle 62. Pin, bolt, or rivet 79 attaches the jaws to member 60. Handle 62 includes handle members 52 and 54 that are normally biased apart by spring 56. Hinge pin 58 allows handle member 54 to move toward handle member 52 as the handle is squeezed.

Figure 4B:
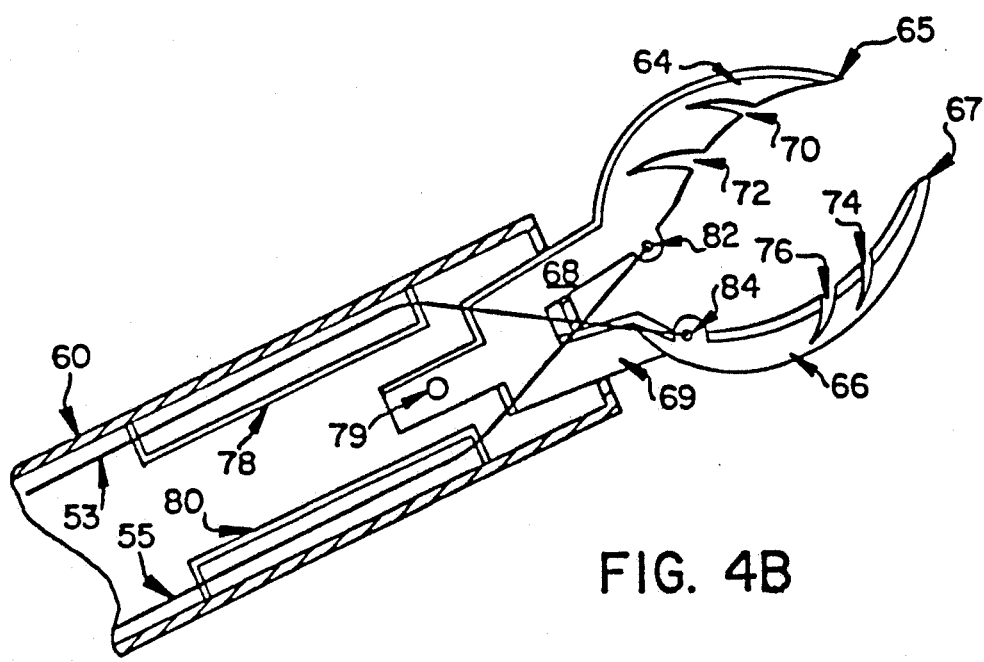
FIG. 4B is a close-up view of the jaws of the tool of FIG. 4A.

The action of the opening and closing of the jaws of the instrument can be more clearly seen in FIG. 4B. Jaws 64 and 66 are formed from spring steel member 68. Wires 53 and 55 are attached to jaws 66 and 64 at points 84 and 82, respectively, and are separated by running them through channels 78 and 80 attached to the inside of tubular member 60. Wires 53 and 55 are pulled taut when the handle member is squeezed. This causes the jaws to close. The clip is held firmly in place in the jaws as it is inserted in the tissue by providing notches 70 and 72 in jaw 64 and notches 74 and 76 in jaw 66 that are shaped to hold the clip barbs. Insertion is further facilitated by sharpened tips 65 and 67, which pierce the tissue just ahead of tips of the clip.

In operation, a clip such as clip 10, FIG. 1, is inserted in the open jaws 64 and 66. Barbs 18 and 20 fit in slots 70 and 72. Barbs 22 and 24 fit in slots 74 and 76. The tip of the clip is located very close to tips 65 and 67 of jaws 64 and 66, respectively. When the jaws are in place against the two sides of the torn tissue being repaired, the instrument is moved forward and handle 62 is squeezed. This pushes the legs of the clip into the tissue and moves the legs together as the clip is inserted. The jaws of the instrument are preferably made slightly offset as shown so that they overlap when completely closed. In that case, when the clip is completely inserted its legs are crossed as they are in FIG. 3.

Whether the clip legs are crossed or not, they are completely embedded within the tissue. This is advantageous because the rigid leg material could irritate the tissue surrounding the area being repaired as the prior art surgical clips have done in other parts of the body. Once the clip is inserted, the jaws are backed out of the tissue and the instrument is removed from the patient. The instrument can then be used to insert another clip in the torn tissue.

Figure 4C:
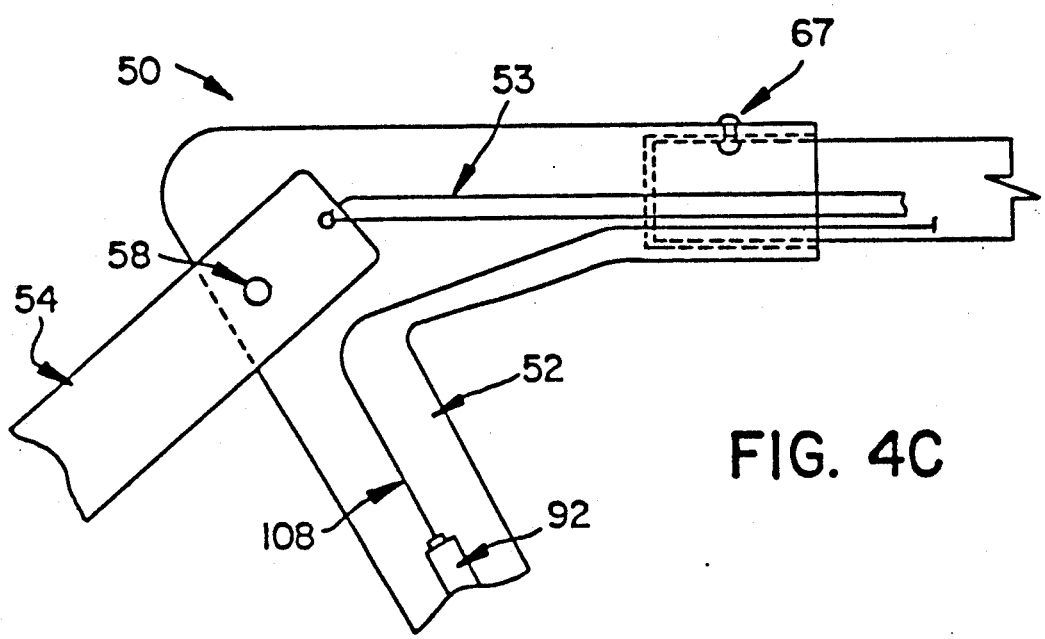
FIG. 4C is a partial cross-sectional view of the handle, trigger and actuating member of the tool of FIG. 4A.

The operation of the handle member to open and close the jaws is shown more clearly in FIG. 4C. Tubular member 60 is attached to handle member 52 by rivet 57. Wires 53 and 55 are attached to handle member 54, which pivots on pin 58 when handles 52 and 54 are squeezed together. As handle 54 moves toward handle 52, it pulls wires 53 and 55 back, which pulls the jaws together and causes them to close. Since the jaws are normally biased apart, when the handle members are released, wires 53 and 55 are relaxed, and the jaws open to release the clip. Wire 108 is attached to sliding switch 92, which pulls wire 108 when it is slid in the direction of the arrow to release the clip as fully explained below in conjunction with FIG. 6.

Figure 4D:
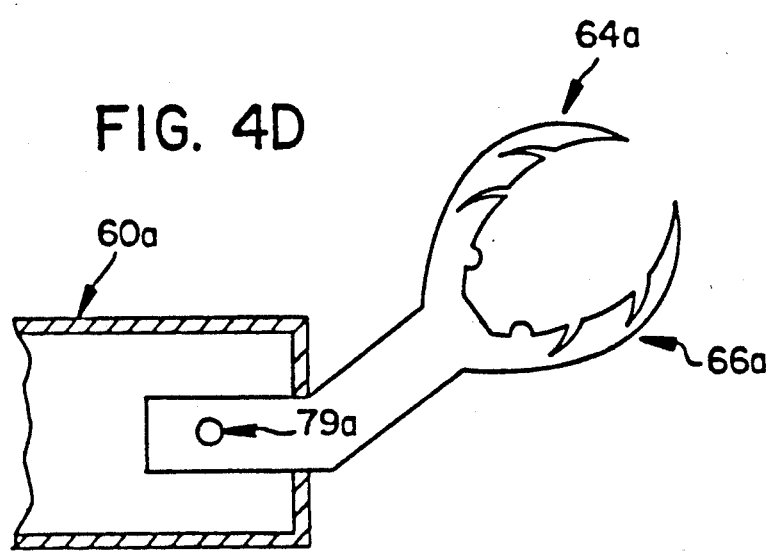
FIG. 4D is a diagrammatic view of an angled jaw for the tool of FIG. 4A.

An alternative way of forming the jaws of the arthroscopic instrument is shown in FIG. 4D. Jaws 64a and 66a are formed at a 30 degree angle to tubular member 60a. Pin, rivet, or bolt 79a attaches the jaws to the tubular member.

Preferably, at least three insertion tools with jaws at different angles are available. One with jaws aligned with the tubular member, one with jaws turned down at approximately 15 degrees, and one with jaws turned down at approximately 30 degrees. This allows the physician to place the clip exactly as desired, depending on the location of the tear, utilizing the same arthroscopic portal during repair.

Figure 5:
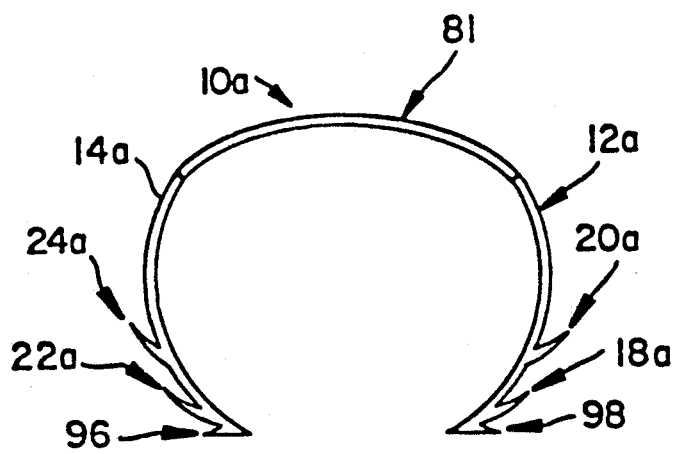
FIG. 5 is an elevational view of an alternative arthroscopic clip according to this invention.

Another way of forming the arthroscopic clip is shown in FIG. 5. Clip 10a includes barbed legs 12a and 14a formed of a rigid biodegradable material, for example a polyglycolic acid polymer. Barbs 18a, 20a, 22a and 24a are fully embedded within the tissue being repaired and do not interfere with joint movement. Tip barbs 96 and 98 allow clip 10a to grip the meniscus so it stays embedded when the jaws are pulled back and out of the patient. This is more clearly shown in FIG. 6. Flexible section 81 is made an intergral part of clip 10a, but is preferably made from a relatively soft, flexible biodegradable material which allows the clip to bend as it is inserted so the legs can be fully embedded in the tissue. A preferred material of the flexible clip is 2.0 Dexon suture. Since interconnecting section 81 is the only section of the clip that is exposed from the meniscus after the clip is inserted, the soft material also provides a clip that is less irritating to the surrounding cartilage than the typical stiff or metallic clips would be and which would not be able to be used intra-articularly.

Figure 6:
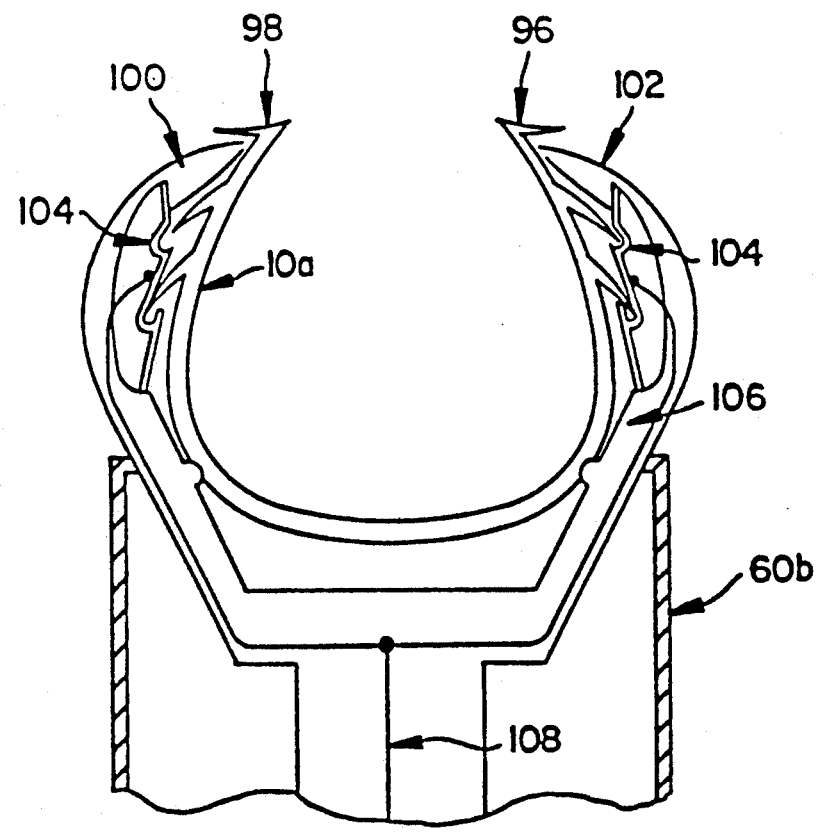
FIG. 6 is an elevational view of an alternative to the jaws of FIG. 4A.

Another way of forming the jaws to ensure proper insertion of clip 10a is shown in FIG. 6. Jaws 100 and 102 are formed to hold the barbs of clip 10a while the clip is being inserted and to release the clip after insertion so that it remains in place embedded in the meniscus. Barb-holding members 104 are spring steel members with small indentations shaped to fit and hold the clip barbs. Wire 106 is attached to members 104. Wire 108 connects wire 106 to switch 92, FIG. 4A.

When clip 10a is fully inserted in the meniscus, the physician operates switch or lever 92. Switch operation pulls on wire 108, FIG. 6, which in turn pulls wire 106. Wire 106 is attached to the underside of members 104. As wire 106 is pulled tight, it pulls members 104 down away from clip 10a. This frees the barbs and leaves them embedded in the meniscus. Insertion barbs 96 and 98 also may be included to help hold clip 10a in place by gripping the tissue just enough to allow clip 10a to separate from jaws 102 and 100 as the jaws are opened and backed out of the meniscus. In conjunction with members 104, insertion barbs 96 and 98 prevent clip 10a from not properly separating from the instrument as it is removed from the mensicus.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A method for repairing a tear in the meniscus comprising:
providing a staple having a pair of legs joined together by a flexible suture material;
inserting the staple into the meniscus so the suture material overlies the tear; and
bending the staple legs inwardly towards each other.

2. A method as in claim 1, wherein said staple legs and said suture material are biodegradable.

3. A method of repairing a tear in the meniscus comprising:
providing a staple having a pair of legs joined together by a flexible material; and
inserting the staple into the meniscus so the flexible material overlies the tear.

4. The method of claim 3, wherein the staple legs are composed of a biodegradable material.

5. The method of claim 4, wherein the flexible material is a biodegradable suture material.

6. The method of claim 3, wherein said legs are composed of a rigid material.

7. The method of claim 6 wherein each said leg includes at least one tissue retaining barb.

8. The method of repairing a tear in the meniscus comprising:
providing an instrument having a pair of opposed jaws;
placing a staple having a pair of legs joined by a suture material in said jaws so each staple leg is received in the notch formed in each jaw;
inserting the instrument in the body to position the jaws over the tear;

squeezing said handles of the instrument to close the jaws; and releasing the staple from the jaws so that the flexible material overlies the tear.

9. The method of claim 8, wherein the staple is composed of biodegradable material.

10. The method of claim 9, wherein each staple leg has an integral tissue retaining barb and said barb is positioned in the notch of the jaw.

11. The method of claim 10, wherein the step of releasing the staple comprises pulling a wire to actuate barb holding members to disengage the instrument from the barbs.

* * * * *